United States Patent [19]  [11] 4,405,633
Brown et al.  [45] Sep. 20, 1983

[54] METHOD OF TREATMENT OF ASTHMA

[75] Inventors: Richard E. Brown, East Hanover, N.J.; Bernard Loev, Scarsdale; Vassil St. Georgiev, Rochester, both of N.Y.

[73] Assignee: USV Pharmaceutical Corporation, Tarrytown, N.Y.

[21] Appl. No.: 353,307

[22] Filed: Mar. 1, 1982

[51] Int. Cl.$^3$ .............................................. A61K 31/42
[52] U.S. Cl. .................................................. 424/272
[58] Field of Search ........................ 424/272; 548/217

[56] References Cited

U.S. PATENT DOCUMENTS 3,895,022  7/1975  Möller et al. .................... 260/307 D
4,298,742 11/1981  Brown et al. ........................ 548/152

Primary Examiner—Leonard Schenkman

[57] ABSTRACT

Provided is a method of treating asthma. The method is the administering to a patient requiring treatment of an effective dose of a benzoxazole-2-carboxylic acid or an ester or therapeutically-acceptable salt of benzoxazole-2-carboxylic acid.

4 Claims, No Drawings

METHOD OF TREATMENT OF ASTHMA

BACKGROUND OF THE INVENTION (1) Field of the Invention

This invention relates to a new method of asthma treatment, more particularly, to the use in the treatment of asthma of certain heterocyclic esters.

(2) Prior Art

Benzoxazole-2-carboxylic acid esters have been described in the literature. For example, esters wherein the esterifying group is alkyl, phenyl, chlorophenyl and allyl including such esters as are substituted in the benzenoid ring with such groups as alkoxy, nitro, alkyl, phenyl and chloro, are described in *Lieb. Ann. Chem.* 733, 70–87 (1970); ibid 749, 1–11 (1971); German Offenlegungschrift 2,164,851; and *J. Chem. Soc. Chem. Comm.* 24, 962-3 (1975).

It has now been surprisingly found that certain esters of benzoxazole-2-carboxylic acid have potent anti-asthmatic activity.

SUMMARY OF THE INVENTION

The esters used in this invention are represented by the following formula:

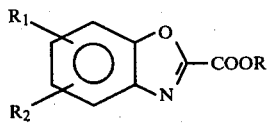

wherein, $R_1$ and $R_2$ are independently H, halo, $C_1$–$C_7$ alkyl, $C_3$–$C_7$ alkoxy, $C_3$–$C_7$ cycloalkyl, hydroxy, cyano, $C_1$–$C_7$ carbalkoxy, nitro, trifluoromethyl, or $R_1$ and $R_2$ together can form a methylenedioxy group; and R is hydrogen, branched or unbranched $C_1$–$C_{12}$ alkyl, $C_3$–$C_{12}$ cycloalkyl or pharmaceutically acceptable salt.

DETAILED DESCRIPTION OF THE INVENTION

The benzoxazole esters used in this invention may be prepared in a two-step synthesis from corresponding benzoxazinediones of the following formula:

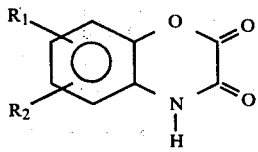

by reaction with thionyl chloride to give the chloro derivative

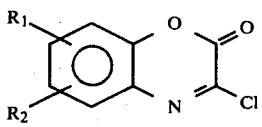

which on reaction with ROH provides the new benzoxazole esters of this invention.

The esters of the invention can also be prepared by ester interchange employing ROH with the corresponding lower alkyl ester, e.g., methyl or ethyl ester.

The starting heterocyclic compounds for the foregoing preparative procedures are known compounds or are preparable by known procedures.

Using the appropriate alcohols with corresponding starting compounds, a wide variety of benzoxazole esters can be prepared.

The present new method of treatment of asthma uses heterocyclic esters which are therapeuticlly useful as such or can be employed in the form of salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present esters.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

The present compounds form conjugates with amino acids and the sugar acids. For example, conjugates can be formed with glucuronic acid, e.g., β-D-glucuronic acid, as well as amino acids especially alpha amino acids, such as glycine, lysine, cystine, methionine, aspartic acid, alanine and the like. The conjugates with pharmaceutically-acceptable amino acids and glucuronic acid are especially useful in formulation of therapeutic dosage forms.

As therapeutic agents, the present heterocyclic esters act via inhibition of mediator release. These esters are active orally in the passive cutaneous anaphylaxis (PCA) screen; and inhibit histamine release from passively sensitized rat mast cells.

The therapeutic agents used in the present invention may be administered alone or in combination with pharmaceutically-acceptable carriers, the proportion of which is determined by the solubility and chemical nature of the compound, chosen route of administration and standard pharmaceutical practice. For example, they can be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He or she will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other antiasmatic agents and the dosage level is of the same order of magnitude as is generally employed with these other therapeutic agents.

The following examples further illustrate the invention.

EXAMPLE 1

A known method of making these compounds is shown in the following:

A. 3,6-Dichlorobenzoxazine-2-one

A mixture of 80.5 of 6-chlorobenzoxazin-2,3-dione, 40 ml of thionyl chloride, 15 ml of dimethyl formamide (DMF) and 1.5 l. of toluene was refluxed with stirring for 5 hours. The reaction mixture was filtered hot and the filtrate concentrated to a gum. Recrystalliztion from toluene gave product, m.p. 136–138° C.

B. Hexyl 5-chlorobenzoxazole-2-carboxylate

A mixture of 36 g of the product of Part A and 13.7 g $Na_2CO_3$ in 250 ml of hexanol was heated at 70° C. for 14 hours. The solvent was evaporated and the residue extracted with ethyl acetate (200 ml). The solution was washed with water, dried, decolorized with charcoal and then evaporated to dryness. The residue was recrystallized from ethyl acetate-hexane to give crystalline product, m.p. 42–43° C.

EXAMPLE 2

The compounds shown in the following table were shown to be useful in the treatment of asthma when screened according to the Rat Passive Cutaneous Anaphylaxis Screen described by I. Mota, Life Sciences, 7 465 (1963) and Z. Ovary, et al., Proceeding Society of Experimental Biology and Medicine, 81, 548 (1952).

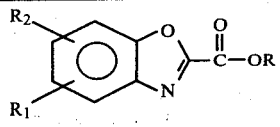

| | | PCA, % I, mg/kg | | | | |
|---|---|---|---|---|---|---|
| | | i.p. | | | p.o. | |
| $R_1$ | R | 10 | 50 | 1 | 10 | 100 |
| H | $C_2H_5$ | 84 | | | | |
| H | $CH_3$ | 87 | | | | |
| H | $n\text{-}C_4H_9$ | 62 | | | | |
| Cl | H | | | 20 | 32 | 75 |
| Cl | Na | | | 16 | 46 | 79 |
| Cl | $n\text{-}C_4H_9$ | | | 28 | 57 | 67 |
| Cl | $t\text{-}C_4H_9$ | 30 | | | 17 | |
| Cl | $CH_2\phi$ | 49 | | | | |
| Cl | $O\text{-}CH(CH_3)\text{-}CH_2\text{-}CH_2\text{-}CH(CH_3)\text{-}CH_3$ | 44 | | | | |
| Cl | 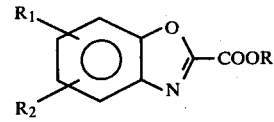 | 28 | | | | |
| Cl | $n\text{-}C_8H_{17}$ | | | 23 | 30 | 55 |
| Cl | $n\text{-}C_6H_{13}$ | | | 24 | 22 | 60 |
| Me | $n\text{-}C_4H_9$ | | | 21 | 34 | 77 |

$R_2$ is hydrogen.

We claim:

1. A prophylactic method for treating an asthmatic patient comprising administering to said patient an effective dose of benzoxarole-2-carboxylic acid or ester having the formula $$\text{[structure: benzoxazole with } R_1, R_2 \text{ substituents and } -COOR]$$

or pharmaceutically acceptable salts thereof, wherein
$R_1$ and $R_2$ are independently H, halo, $C_1$–$C_7$ alkyl, $C_3$–$C_7$ alkoxy, $C_3$–$C_7$ cycloalkyl, hydroxy, cyano, carboxy, $C_1$–$C_7$ carboalkoxy, nitro, trifluoromethyl or $R_1$ and $R_2$ together form a methylenedioxy group; and
R is H, $C_1$–$C_{12}$ alkyl or $C_3$–$C_{12}$ cycloalkyl.

2. The method of claim 1 wherein $R_1$ and $R_2$ are independently H, halo, $C_1$–$C_7$ alkyl or $C_3$–$C_7$ alkoxy.

3. The method of claim 1 wherein R is hydrogen, $C_1$–$C_{12}$ alkyl or a pharmaceutically acceptable salt.

4. The method of claim 1 wherein $R_1$ is H, chloro or methyl.

* * * * *